United States Patent
Schmitt

(10) Patent No.: US 10,794,981 B2
(45) Date of Patent: Oct. 6, 2020

(54) METHOD AND APPARATUS RECONSTRUCTION OF MAGNETIC RESONANCE IMAGES IN A POSITION DIFFERENT FROM THE ACQUISITION POSITION

(71) Applicant: Siemens Healthcare GmbH, Erlangen (DE)

(72) Inventor: Peter Schmitt, Weisendorf (DE)

(73) Assignee: Siemens Healthcare GmbH, Erlangen (DE)

( * ) Notice: Subject to any disclaimer, the term of this patent is extended or adjusted under 35 U.S.C. 154(b) by 133 days.

(21) Appl. No.: 16/039,456

(22) Filed: Jul. 19, 2018

(65) Prior Publication Data

US 2019/0025394 A1    Jan. 24, 2019

(30) Foreign Application Priority Data

Jul. 19, 2017    (DE) .................. 10 2017 212 398

(51) Int. Cl.
*A61B 5/055*    (2006.01)
*G01R 33/565*    (2006.01)
(Continued)

(52) U.S. Cl.
CPC .......... *G01R 33/565* (2013.01); *A61B 5/0555* (2013.01); *G01R 33/5608* (2013.01);
(Continued)

(58) Field of Classification Search
CPC .............. A61B 5/055; A61B 2034/107; A61B 2090/374; A61B 6/5205; A61B 8/4461; A61B 8/12; A61B 8/4209; A61B 6/032; A61B 6/4035; A61B 6/025; A61B 5/0555; G06T 7/0012; G06T 7/11; G06T 7/70; G06T 2207/30004; G06T 2207/30204; G06T 11/005; G06T 11/006; G06T 11/003; G06T 5/006; G06T 2207/10076; G06T 2207/10088; A61N 5/1049; A61N 5/1067; A61N 5/1037; A61N 5/1039; A61N 5/107; A61N 5/1069; A61N 2005/1051; A61N 2005/1054; A61N 2005/1055; G01R 33/5608; G01R 33/56563;
(Continued)

(56) References Cited

U.S. PATENT DOCUMENTS 4,591,789 A    5/1986    Glover et al.
6,368,285 B1 *  4/2002    Osadchy .............. A61B 5/0064
                                                        382/131
(Continued)

*Primary Examiner* — Andrew M Moyer
*Assistant Examiner* — Dennis Rosario
(74) *Attorney, Agent, or Firm* — Schiff Hardin LLP

(57) ABSTRACT

A magnetic resonance system is operated in a preliminary examination so as to acquire magnetic resonance data while an object undergoing investigation is in a first position relative to the scanner of the magnetic resonance system. Using the first magnetic resonance data, or image data derived therefrom, a processor reconstructs an image of the object. The image has a distortion in relation to the object. The processor presents the image to a person operating the system at a display device. The processor reconstructs the image such that the distortion is determined by a target position that is independent of the position of the object.

13 Claims, 4 Drawing Sheets

(51) Int. Cl.
*G06T 7/11* (2017.01)
*G06T 7/70* (2017.01)
*G01R 33/56* (2006.01)
*G06K 9/32* (2006.01)
*G06T 11/00* (2006.01)
*G06K 9/36* (2006.01)

(52) U.S. Cl.
CPC ............ *G06K 9/3233* (2013.01); *G06T 7/11* (2017.01); *G06T 7/70* (2017.01); *G06T 11/008* (2013.01); *G06K 2009/363* (2013.01); *G06T 2207/10088* (2013.01)

(58) Field of Classification Search
CPC ............ G01R 33/56509; G01R 33/543; G01R 33/56518; G01R 33/5616; G01R 33/5673; G01R 33/56572; G01R 33/56; G01R 33/565; G01R 33/5659; G01R 33/56545; G06K 2009/363
See application file for complete search history.

(56) References Cited

U.S. PATENT DOCUMENTS

| | | | |
|---|---|---|---|
| 7,088,099 B2 | 8/2006 | Doddrell et al. | |
| 8,854,037 B2 | 10/2014 | Feiweier | |
| 9,000,767 B2 * | 4/2015 | Schmidt | G01R 33/34084 324/318 |
| 9,269,140 B2 * | 2/2016 | Machado | A61B 5/0042 |
| 2006/0012365 A1 | 1/2006 | Werthner | |
| 2008/0068012 A1 | 3/2008 | Werthner | |
| 2008/0123910 A1 * | 5/2008 | Zhu | A61B 90/36 382/128 |
| 2015/0146999 A1 | 5/2015 | Feiweier et al. | |
| 2016/0078616 A1 * | 3/2016 | Horger | G06K 9/46 382/131 |
| 2016/0338614 A1 * | 11/2016 | Gall | A61B 5/0555 |
| 2018/0333069 A1 | 11/2018 | Paul et al. | |

* cited by examiner

METHOD AND APPARATUS RECONSTRUCTION OF MAGNETIC RESONANCE IMAGES IN A POSITION DIFFERENT FROM THE ACQUISITION POSITION

BACKGROUND OF THE INVENTION

Field of the Invention

The present invention concerns a method and apparatus for determining an image of an object using magnetic resonance (MR) data that have been acquisitioned using an MR scanner in a preliminary examination during which the object was positioned in a position relative to the MR scanner, wherein, using the MR data or image data derived therefrom, a processor reconstructs the image of the object, wherein the image has a distortion in relation to the object, and wherein the processor presents the image for viewing at a display screen.

Description of the Prior Art

When an object (frequently a person) is examined in a magnetic resonance system, spatial encoding is generally carried out by magnetic field gradients being temporarily overlaid on a static and substantially homogeneous basic magnetic field. Overlaying the magnetic field gradients is frequently performed while nuclear spins in the object are excited so as to cause them to emit MR signals. The excitation of the nuclear spins is the result of radio frequency (RF) pulses being radiated so as to act on the object (so-called slice-selective excitation). The MR signal that is obtained may be analyzed, for example, with regard its frequency content (MR spectroscopy) or, with the use of further gradients, can be spatially encoded in further spatial directions. With perfectly linear field gradients, the spatial encoding of the acquired MR data is likewise be linear. In practice, however, the magnetic field gradients that are actually generated differ from the ideal. Typically, the farther away the signal-producing nuclear spins are from the center of the magnetic gradient coil system (which is conventionally identical to the center of the basic field magnet that generates the static basic magnetic field), the greater the error. An intermediate image that is reconstructed using the acquired MR data without further correction will then exhibit distortion. Such distortion of the object depends on the position of the object undergoing investigation relative to the center of the magnetic gradient coil system. The acquisitioned MR data represent an image of the actual object as "seen" by the gradient coil system, so to speak.

The situation described above is generally known to those skilled in the field of MR imaging. Images of this kind, reconstructed without further correction, are commonly called ND images, wherein the abbreviation "ND" stands for "non-distortion corrected". The abbreviation "ND" is also used in this sense below.

Quantification of the imaging errors caused by the distortion, and the distortion caused thereby, is known in many cases. It is thus possible to correct ND images of this kind. The correspondingly corrected images are commonly called DIS images, wherein the abbreviation "DIS" stands for "distortion corrected". The abbreviation "DIS" is also used in this sense below. Accordingly, it is possible to match, with each image point (pixel or voxel) in the ND image, the corresponding image point on the DIS image, and vice versa. This is done by a suitable description of the magnetic field gradients with the use of multi-dimensional mathematical functions and a suitable transformation. Both the description of the magnetic field gradients and suitable transformations are known to those skilled in the field of MR imaging. Examples of such techniques are described in U.S. Pat. Nos. 4,591,789 A and 7,088,099 B2.

Distortion is substantially independent of the object itself that is under examination, and is dependent only on the position of the object relative to the magnetic resonance scanner (and hence the position relative to the center of the magnetic gradient coil system or the basic magnet). It is therefore important for the correction that the position of the object undergoing investigation relative to the magnetic resonance system be known. This position may vary from one scan to the next, since in magnetic resonance scanners the patient table on which the object is located is movable in the direction of the longitudinal axis of the basic magnetic field (typically designated the z direction). Consequently, as seen in the z direction, the object undergoing investigation may be positioned in almost any desired way relative to the magnetic resonance scanner. For positioning in the z direction, the term "table position" is frequently also used.

DE 10 2013 224 406 B4 and U.S. Pat. No. 8,854,037 B2 disclose methods for correcting distortion in MR imaging.

The correction has a one-to-one correspondence, meaning that, in principle, it is possible to reverse the transformation and to reconstruct the associated ND image again from a DIS image. This is done in practice in some cases.

In practice, MR data are often first acquisitioned in a preliminary examination (scout scan), and an image of the object undergoing investigation is then reconstructed from that data. In some cases, this image is a DIS image, and in other cases it is an ND image.

It is possible, using the MR data acquisitioned in the preliminary examination, to reconstruct a distortion corrected image (DIS image) and then to use this image to carry out further planning, in particular to specify to the processor, using appropriate marking, a region to be investigated in the course of the subsequent diagnostic examination (scan) and excitation of the region to be investigated is thereby designated and set in the diagnostic imaging parameters.

This is indeed frequently the conventional procedure. In the course of planning of this kind, the assumption is made that distortions that occur are not too pronounced, and that the field of view (FOV) that is actually acquisitioned later in the diagnostic scan is in sufficient agreement with the desired region.

When planning using DIS images, the images are independent of the table position that existed when the MR data that form the basis of the images were acquisitioned. This is still true if a number of images are being utilized at the same time.

Typically, planning using DIS images is acceptable if a relatively small target volume lies close to the isocenter of the magnetic resonance scanner, with the result that the expected distortions and position offsets are relatively small. These are also acceptable when the area covered by the target volume is so large that any inaccuracies are insignificant.

Planning using DIS images still can be problematic, since the distortion is already relevant in the context of the selective excitation. If a straight slice or a cubic volume is specified in a DIS image by the marking, it is not possible to excite spins in that precise slice or volume. Rather, as a result of the distortion, spins in a curved slice or distorted cube are excited. Moreover, the slice or cube may be (and indeed typically is) spatially offset with respect to the slice or cube that is actually selected. At the time of generating the MR data, therefore, the object undergoing investigation is already "seen" from the context of the gradient coil system by the system. Thus, planning of an "ideal" slice or cube based on the undistorted object undergoing investigation would not reflect which slice or cube would actually be excited for the purpose of emitting diagnostic MR signals.

In some cases, the error caused by this factor is acceptable. In other cases, the error caused thereby cannot be tolerated. This may be the case particularly when regions of the object undergoing investigation that are far away from the axis of symmetry of the MR scanner are to be excited for the purpose of emitting diagnostic MR signals. Examples of regions of this kind are the hand or shoulder of the object undergoing investigation.

If the diagnostic examination is planned on the basis of a DIS image, it may occur that the volume that is in fact excited for the purpose of emitting diagnostic MR signals differs markedly from the volume that was previously selected using the DIS image. This may be critical particularly if the region selected is to be acquisitioned by spectroscopy. This is because, in this case, it is no longer possible to infer from the acquisitioned signals from which region they originate. It is thus no longer possible to identify erroneous excitation of the "wrong" region. Consequently, it is important to ensure reliably that the "right" region is indeed excited. When small regions are acquisitioned (for example when imaging a hand), it may furthermore be the case that the MR data emitted in the course of the diagnostic examination no longer represent an image of the volume that is actually desired.

For the purpose of eliminating errors of this kind, the region to be investigated in the course of the diagnostic examination and the selected excitation of the region to be investigated are therefore sometimes specified on the basis of the corresponding ND image. As mentioned, this image can be reconstructed, and indicates the region that is actually selected for the purpose of emitting diagnostic MR signals. However, distortion of the image in which the region to be investigated is established must be in exact agreement with the distortion that occurs in the course of the diagnostic examination when the magnetic resonance data are acquisitioned.

In the prior art, the ND image is always reconstructed for the table position at which the MR data were acquisitioned in the course of the preliminary examination. Consequently, in the prior art the MR data must also be acquisitioned in the same table position in the course of the diagnostic examination. This restriction may have the result that only MR data of suboptimal quality can be obtained, since the region to be investigated is a long distance from the center of the MR scanner. If other measurements in other table positions have previously been performed, these measurements are no longer compatible with the ND image that is now used for planning the diagnostic examination. This is disadvantageous because simultaneous planning, using a number of series, for example with different contrasts (T1, T2, diffusion, contrast-enhanced, etc.), may be desirable. This restriction is particularly disadvantageous if not only images of rapid measurements without further restrictions are to be utilized for planning, but also images of relatively long measurements or measurements that can be performed only directly after a contrast agent has been injected.

SUMMARY OF THE INVENTION

An object of the present invention is to provide precise and spatially correct planning of the diagnostic examination in a simple and reliable manner.

According to the invention, a determination method of the type described initially has the further feature of the processor reconstructing the image from the MR data acquired in the preliminary scan such that the distortion is determined by a target position that is independent of the position of the object in the preliminary scan.

The invention makes it possible to generate an ND image for a (in principle, for any desired) target position of the object undergoing investigation, regardless of whether the target position is in agreement with the position from which the preliminary MR data were acquisitioned. This makes it possible to determine the target position such that it is in agreement with the position in which the region of the object that is to be investigated in the diagnostic examination is, relative to the magnetic resonance scanner. In the course of the later diagnostic examination, it is thus also possible to position the object undergoing investigation in a manner corresponding to this target position.

The invention is based on the insight that the restriction on determining an ND image, which was universally imposed in the prior art, to the table position in which the MR data on which the ND image is based were acquisitioned is an unnecessary restriction. Rather, using the MR data, first an ND image can be determined for the table position at which the MR data were acquisitioned. However, because the ND image can also be used to determine the associated DIS image, then, based on this DIS image, the associated ND image for any desired table position can be determined.

Preferably, the target position is established by the processor using the acquisitioned preliminary MR data to reconstruct an intermediate image, and presenting the intermediate image to the person operating the system for viewing at a display screen, with the processor receiving, from the person operating the system, a marking in the intermediate image that determines the target position. As a result, it becomes particularly simple to specify the target position. The processor can reconstruct the intermediate image such that it has no distortion in relation to the object undergoing investigation. Alternatively a reconstruction by the processor can be implemented in which the intermediate image has a distortion determined by the position that existed in the preliminary scan. The marking, if required, can be a point, a line at right angles to the direction in which the patient table can be positioned, or a planar region.

Moreover, planning can be further optimized by, using the marking received from the operator in the displayed intermediate image, the processor determining a region and then the processor determining the target position using the region determined using the marking. Alternatively, operator can directly mark the aforementioned region instead of the processor determining that region. For example, the processor may determine the centroid of the marked region in the intermediate image, and determine the target position such that the centroid is positioned in the optimum manner. Depending on the type of the marking, determining the corresponding region may or may not be a trivial matter. For example, if the marking is a point and the associated region in the intermediate image is precisely the point defined by the marking, then all that needs to be done is to image this point in a second intermediate image.

As an alternative to the operator specifying the target position, it is possible for the processor to determine the target position autonomously, using at least the MR data from the preliminary scan. For example, the processor may determine anatomical structures of a person undergoing investigation from that MR data, and determine the target position from the identified anatomical structures.

As a result of the procedure according to the invention, it is also possible to carry out planning simultaneously on a number of images that have each been reconstructed using respective magnetic resonance data, wherein the object undergoing investigation has been positioned at the time of capturing the respective magnetic resonance data at a respective position. It is thus possible to carry out planning on a number of ND images that have all been determined for the same table position even though the underlying magnetic resonance data were acquisitioned at different table positions. Then, the aforementioned preliminary examination is a first preliminary examination in which first magnetic resonance data are acquired at a first position relative to the magnetic resonance scanner, and the aforementioned intermediate image is a first intermediate image. It is thus possible for the processor

- to reconstruct a second intermediate image using second magnetic resonance data that were acquisitioned by the magnetic resonance system in the course of a second preliminary examination, while the object undergoing investigation was positioned in a second position, independent of the first position, relative to the magnetic resonance scanner,
- to present the second intermediate image to the person operating the system for viewing at the display screen, in addition to the first intermediate image, and
- to determine a second marking for the second intermediate image, corresponding to the first marking in relation to the object undergoing investigation, and to overlay the second marking onto the second intermediate image.

Preferably, the processor reconstructs the second intermediate image analogously to the first intermediate image, i.e., such that it either has no distortion in relation to the object undergoing investigation, or has a distortion determined by the second position.

Where the intermediate images are intermediate images with a distortion, the intermediate images show the object undergoing investigation with a respective distortion, which may be individual to the respective intermediate image. However, this only applies until the target position is specified. Once the target position is specified, the representations are preferably harmonized. Thus, using the second magnetic resonance data or image data derived therefrom, the processor reconstructs the second image of the object undergoing investigation that, like the first image of the object undergoing investigation, has a distortion, determined by the target position, in relation to the object undergoing investigation, and presents the second image to the person operating the system at the display screen, in addition to the first image. This makes it possible to reproduce, in a mutually compatible manner, ND images that were acquisitioned in different positions, with the result that planning using all these similarly distorted images becomes possible.

For simplifying planning, the processor furthermore preferably adopts markings, which were specified for the first image, in the second image.

Preferably, the processor receives a marking from the operator, in the first image or another image, of a region to be investigated in the course of the diagnostic examination, and a specified excitation of the region to be investigated. As a result, planning the diagnostic examination becomes particularly simple. In some circumstances, it is even possible for the target position to undergo another offset as a result of specifying the region to be investigated. Depending on the situation in an individual case, it may be useful to permit unlimited offset of the target position or to restrict the offset of the target position to a narrow range, for example only within the region to be investigated.

The present invention also encompasses a magnetic resonance imaging system having a magnetic resonance scanner operated by a control computer or computer system, wherein the control computer or computer system is configured to operate the magnetic resonance scanner so as to implement any or all embodiments of the method according to the invention, as described above.

The present invention also encompasses a non-transitory, computer-readable data storage medium encoded with programming instructions (program code) that, when the storage medium is loaded into a computer or computer system of a magnetic resonance imaging apparatus, cause the computer or computer system to operate the apparatus in order to implement any or all embodiments of the method according to the invention, as described above.

The object is furthermore achieved by a determination method for magnetic resonance data of an object undergoing investigation, when the target position of the object undergoing investigation relative to the MR scanner, the region to be investigated, and the selected excitation of the region to be investigated, are determined based on the result of any of the embodiments described above.

DESCRIPTION OF THE PREFERRED EMBODIMENTS

Figure 1:
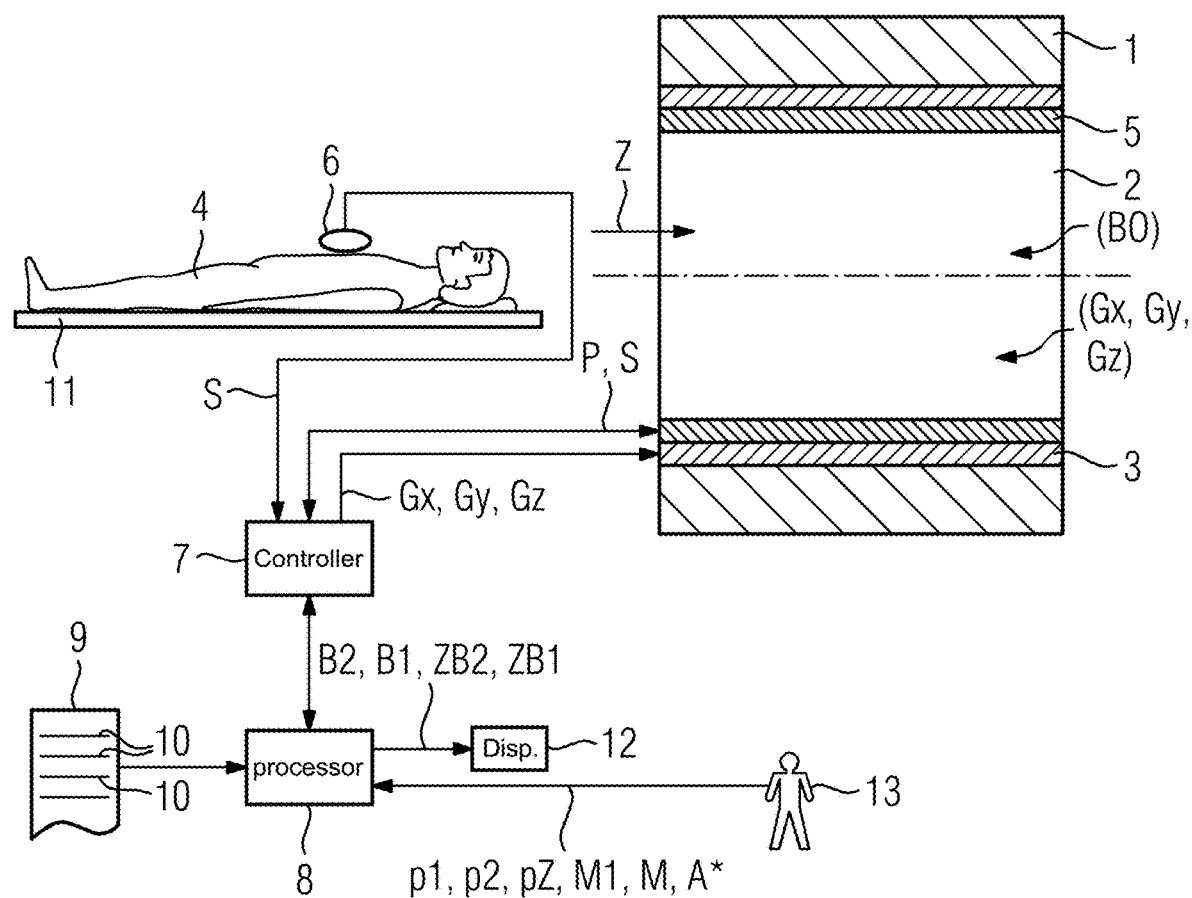
FIG. 1 schematically illustrates a magnetic resonance system.

According to FIG. 1, a magnetic resonance system has scanner with a basic field magnet 1 that generates, in an examination volume 2, a basic magnetic field B0 that is static over time and substantially homogeneous in space. The basic magnetic field B0 has a strength of, for example 1.5 tesla or 3 tesla. The magnetic resonance system further has a magnetic gradient coil system 3. Using the magnetic gradient coil system 3, field gradients Gx, Gy, Gz can be overlaid on the basic magnetic field B0. By applying the magnetic field gradients Gx, Gy, Gz in time-coordinated manner, a spatially selective excitation by radio frequency (RF) pulses and/or a spatial encoding of RF pulses P, and/or magnetic resonance signals S that are excited by the RF pulses P, can be achieved. The magnetic resonance system further has an RF system that generates the RF pulses P. The RF pulses P excite nuclear spins in an object 4 undergoing investigation located in the examination volume 2, for the purpose of emitting the magnetic resonance signals S. The magnetic resonance signals S are received by the RF system. Typically, the RF system includes at least one whole body coil 5. It may additionally include local coils 6. The magnetic resonance system (including the reception of the magnetic resonance signals S) is controlled by a controller 7. The corresponding construction, operation and operating principle of a magnetic resonance system of this kind and the associated controller 7 are generally known to those skilled in the art.

Figure 2:
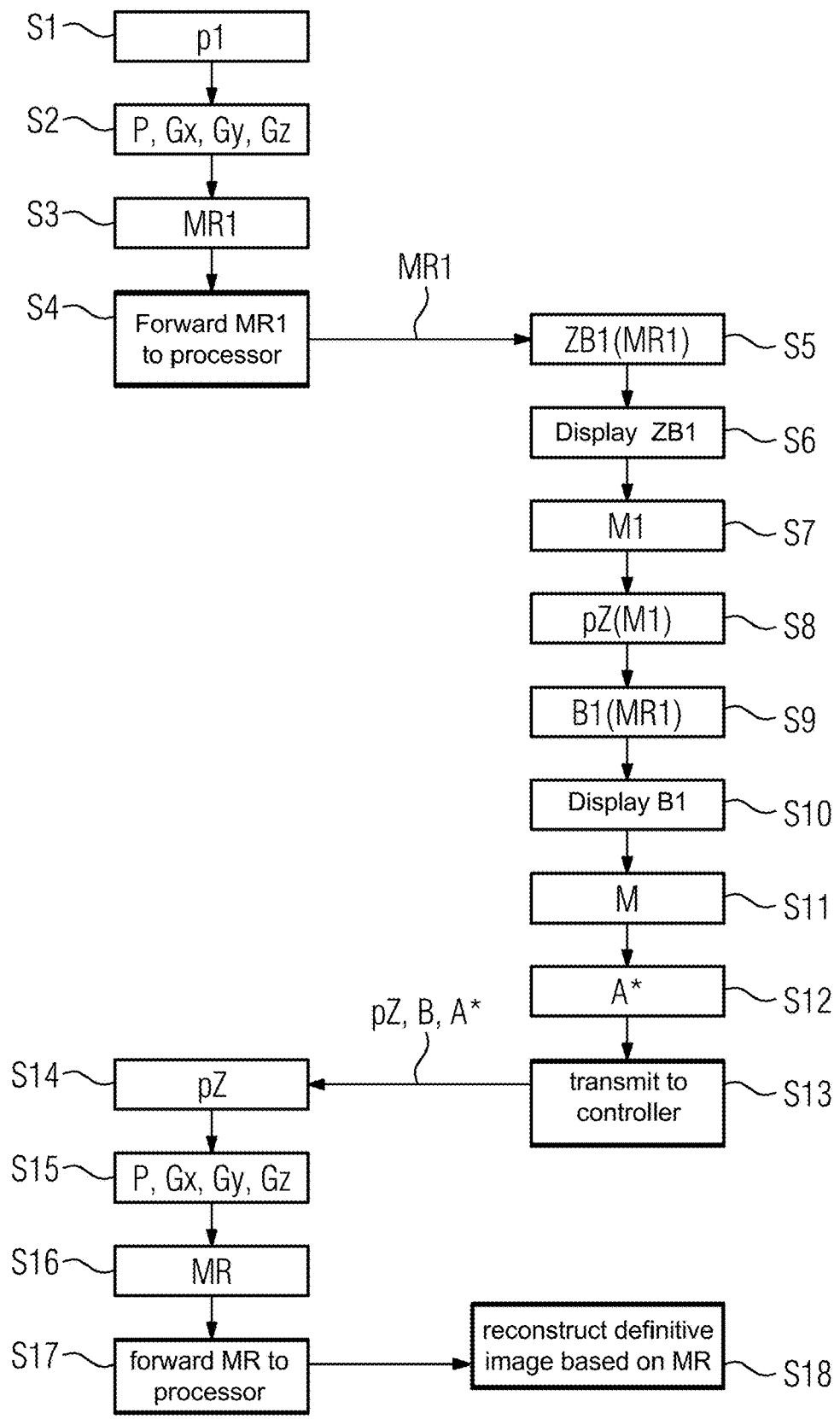
FIG. 2 is a flowchart of an embodiment of the invention.

Typically, the controller 7 is connected to a processor 8. In individual cases, the controller 7 may also be the same as the processor 8. Regardless of whether the processor 8 is a separate device or is the same as the controller 7, the processor 8 is programmed with a computer program 9. The computer program 9 includes machine code 10 that is executed by the processor 8 so that the processor 8 performs the determination method explained in more detail below in conjunction with FIG. 2. Here, the left side in FIG. 2 represents the steps that are not carried out, or need not necessarily be carried out, by the processor 8. The right side in FIG. 2 represents the steps that are always carried out by the processor 8.

Figure 3:
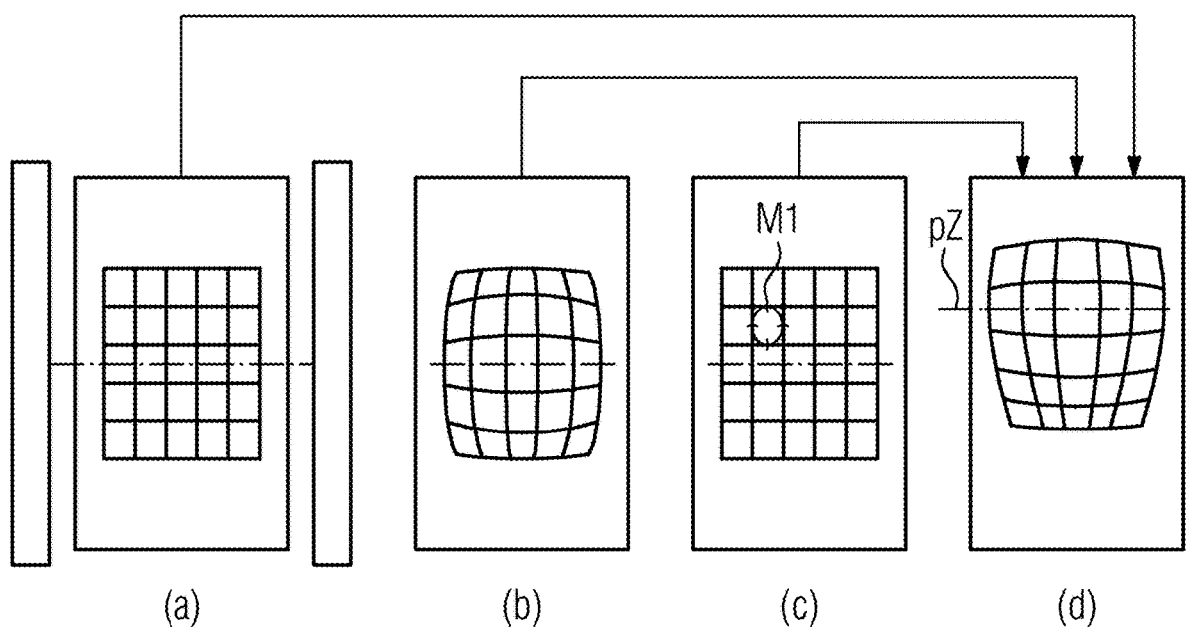
FIG. 3 shows an object undergoing investigation and images of the object undergoing investigation obtained in an embodiment of the invention.

According to FIG. 2, first a preliminary examination of the object 4 undergoing investigation is carried out. For this purpose, in a step S1, the object 4 is put in a first position p1 relative to the MR scanner; cf. the illustration (a) in FIG. 3. For example, a patient table 11 on which the object 4 is located may be offset within a particular range in the z-direction, designated in FIG. 1. The horizontal line in illustration (a) of FIG. 3 is intended to indicate the first position p1.

In many cases, the position in the z-direction is the only possible position. In rare individual cases, however, in addition to the position in the z-direction, a position—albeit only by a small amount—at a right angle to the z-direction may be possible, either in the horizontal or the vertical direction, or in both the horizontal and the vertical directions.

Step S1 may be carried out by the controller 7. As an alternative, however, it may also be carried out manually by a person operating the magnetic resonance system (for example a technician). Then, in a step S2, the controller 7 controls the magnetic resonance system such that the object 4 is excited for the purpose of emitting magnetic resonance signals S. The controller 7 acquisitions the excited magnetic resonance signals S, as first magnetic resonance data MR1, in a step S3, and forwards the first magnetic resonance data MR1 to the processor 8, in a step S4.

In a step S5, the processor 8 reconstructs a first intermediate image ZB1 from the acquisitioned first magnetic resonance data MR1. The processor 8 can reconstruct the first intermediate image ZB1 such that it has a distortion corresponding to the illustration (b) in FIG. 3. This is an ND image. Where there is a distortion, it is determined by the first position p1. As an alternative, the processor 8 may reconstruct the first intermediate image ZB1 such that it has no distortion, corresponding to the illustration (c) in FIG. 3. This is a DIS image. Both procedures are known to those skilled in the art and so there is no need to explain them in more detail herein. The horizontal line in illustrations (b) and (c) of FIG. 3, as in illustration (a) of FIG. 3, designates the first position p1.

In a step S6, the processor 8 presents the reconstructed first intermediate image ZB1, at a display device 12 shown in FIG. 1 (for example an individual monitor or a group of monitors), to a person 13 operating the system, who is likewise shown in FIG. 1. The person 13 operating the system may be a doctor or a radiologist.

Then, a target position pZ is determined for the object 4 relative to the magnetic resonance scanner. For example, the processor 8 may receive the target position pZ from the person 13 operating the system. As an alternative, the processor 8 may determine the target position pZ autonomously, using the first magnetic resonance data MR1. In both cases, the target position pZ can be determined independently of the first position p1. Although it may be in agreement with the first position p1, such an agreement would be purely by chance, and so is not mandatory.

For specifying the target position pZ, in a step S7 the processor 8 may receive a first marking M1 from the person 13 operating the system. The marking M1 may be drawn onto the DIS image by the person 13 operating the system, as in FIG. 3. However, it may likewise be drawn onto the ND image. It may also be specified in another way. When the first marking M1 is specified, the processor 8 determines the target position pZ on the basis of the first marking M1, in a step S8.

For example, the first marking M1 may be a simple cross or similar that determines the target position pZ directly on the first intermediate image ZB1. In this case, step S8 is a trivial matter. As an alternative, in step S8 the processor 8 may first determine a region using the first marking M1 in the first intermediate image ZB1, and then determine the target position pZ using the determined region. For example, the person 13 operating the system may select a region of the object 4 that is represented in the first intermediate image ZB1, for example one or more polygonal, such as rectangular, regions. Using all the selected regions, the processor 8, for example, may determine the weighted or unweighted centroid of the selected regions, or the center of the selected region as a whole. The centroid or center can in this case correspond to the target position pZ.

In a step S9, the processor 8 then reconstructs a first image B1 of the object 4. The reconstructed first image B1 is presented by the processor 8 in a step S10, at the display device 12, to the person 13 operating the system. Here, it is possible for the first image B1 to replace or displace the first intermediate image ZB1. This embodiment is preferred. As an alternative, the first image B1 can be shown in addition to the first intermediate image ZB1.

In relation to the object 4, the first image B1 has a distortion, as shown in illustration (d) in FIG. 3. However, the distortion does not correspond to the distortion determined by the first position p1. Rather, the distortion of the first image B1 is determined by the target position pZ.

It is possible for the target position pZ to be definitively determined the first time step S9 is carried out. As an alternative, it is possible for the person 13 operating the system to change the target position pZ again—taking as a basis the current representation of the first image B1. If the target position pZ is changed, the processing device 8 also adapts the distortion to the changed target position pZ. In some cases, changes in the target position pZ may still be possible to a limited extent after the first time step S9 has been carried out. This may be useful if the first marking M1 was first specified in a DIS image.

As indicated in FIG. 3 by corresponding arrows, the reconstruction in step S9 may be performed by reconstruction from the image data, i.e., from the ND image reconstructed using the first magnetic resonance data MR1, or from the DIS image reconstructed using the first magnetic resonance data MR1. As an alternative, the reconstruction may also be performed directly from the first magnetic resonance data MR1. Those skilled in the art know how the associated ND image may be reconstructed from the acquisitioned first magnetic resonance data MR1 for the first position p1. Furthermore, those skilled in the art know how the associated DIS image may be reconstructed from the ND image that was reconstructed for the first position p1. Moreover, the DIS image can be offset, specifically because the distortions and marks in the DIS image have been corrected, so that another point on the object 4 is situated in the center of the magnetic gradient scanner. Once the DIS image has been offset, however, it can be transformed back into the associated ND image using the transformation known to those skilled in the art.

The procedure explained above serves the purpose of simplifying the planning steps for a main examination that is to be carried out after the first preliminary examination. Thus, the person 13 operating the system specifies a marking M in the first image B1 to the processor 8. The marking M defines a region B that is to be investigated by the magnetic resonance system in the course of the main examination. The processor 8 may receive the marking M in a step S11. As an alternative, the processor 8 may determine the marking M from the first marking M1, in particular adopting the first marking M1 in a one-to-one correspondence. Moreover, the person 13 operating the system specifies to the processor 8 a setpoint excitation A* of the region B to be investigated. The processor 8 receives the setpoint excitation A* in a step S12. In a step S13, the processor 8 transmits the target position pZ, the region B to be investigated (or data characteristic thereof), and the setpoint excitation A* (or data characteristic thereof) to the controller 7.

In a step S14, the object 4 is then positioned at the target position pZ relative to the magnetic resonance scanner. In a manner analogous to step S1, step S14 may be carried out in an automated manner by the controller 7, or manually by the person 13 operating the magnetic resonance system. Next, in a step S15, the controller 7 triggers the magnetic gradient coil system 3 (and also the RF system) such that the region B to be investigated is excited in accordance with the setpoint excitation A* for the purpose of emitting magnetic resonance signals S. Control of the magnetic gradient coil system 3 takes into account the target position pZ of the object 4. In a step S16, the controller 7 acquisitions the associated magnetic resonance signals S as magnetic resonance data MR. It forwards the magnetic resonance data MR to the processing device 8 in a step S17. Finally, in a step S18, the processing device 8 uses the acquisitioned magnetic resonance data MR to reconstruct a definitive image, which is then used by the person 13 operating the system for diagnosis and assessment of the object undergoing investigation 4. This image may be an ND image. Preferably, however, it is a DIS image.

Figure 4:
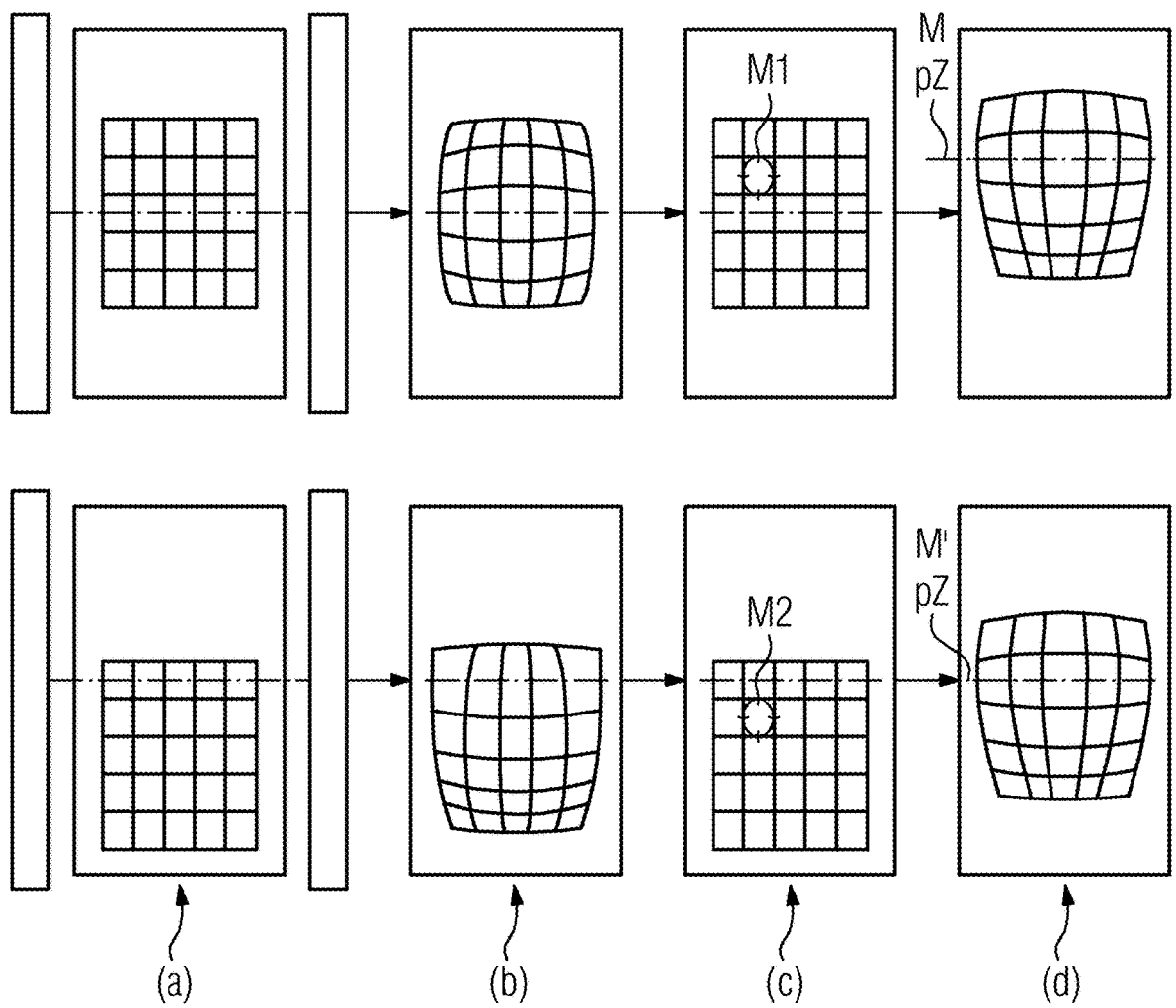
FIG. 4 shows an object undergoing investigation and images of the object undergoing investigation obtained in another embodiment of the invention.

The present invention has been explained above in connection with a single intermediate image ZB1, namely the first intermediate image ZB1. However, as shown in FIG. 4, it may also readily be implemented in connection with a further (at least one) intermediate image ZB2, designated the second intermediate image ZB2 below. In this case, steps S1 to S6 are each carried out separately for each intermediate image ZB1, ZB2. For each intermediate image ZB1, ZB2, the respective position p1, p2 may be determined individually. It is thus possible to distinguish the position p2 for the second intermediate image ZB2 from the position p1 for the first intermediate image ZB1. However, this may also, albeit purely by chance, be the same position p1.

As can be seen from FIG. 4, the processor 8 presents the second intermediate image ZB2 to the person 13 operating the system at the display device 12 in addition to the first intermediate image ZB1. Moreover, the processing device 8 may reconstruct the second intermediate image ZB2, in a manner corresponding to the illustration (b) in FIG. 4, such that in relation to the object 4 it has a distortion determined by the second position p2. As an alternative, the processor 8 may reconstruct the second intermediate image ZB2, in a manner corresponding to the illustration (c) in FIG. 4, such that in relation to the object undergoing investigation 4 it has no distortion. Typically, the intermediate images ZB1, ZB2 are reproduced in the same way. Thus, it is neither possible for the two intermediate images ZB1, ZB2 to have a distortion, or for both the intermediate images ZB1, ZB2 to have a distortion determined by the respective positions p1, p2.

Using the first marking M1 that has been specified or determined for the first intermediate image ZB1, the processor 8 furthermore determines a second marking M2 for the second intermediate image ZB2, and overlays the second marking M2 onto the second intermediate image ZB2. The processor 8 determines the second marking M2 such that it corresponds with the first marking M1 with regards to the object 4. The second marking M2 and the first marking M1 thus mark regions of the object 4 that correspond in the intermediate images ZB1, ZB2.

Moreover, and corresponding to the illustration (d) in FIG. 4, the processor 8 additionally reconstructs a second image B2 of the object undergoing investigation 4. The reconstruction is performed analogously to the first image B1. However, the determination is based on the second magnetic resonance data MR2 or image data derived therefrom (for example the associated ND image or the associated DIS image). Here, it is significant that the second image B2 is an ND image for which the distortion is determined by the target position pZ, which is harmonized for all the images B1, B2. The processor 8 presents the second image B2 in accordance with the illustration in FIG. 4—see the illustration part (d) there—in addition to the first image B1, to the person 13 operating the system, at the display device 12. Moreover, the processor 8 adopts markings M, which have been specified in accordance with the illustrations in FIG. 4 for the first image B1, in the second image B2 (provided with reference numeral M' therein).

In summary, in the present invention, uses a magnetic resonance system, in the course of a preliminary examination, to acquire magnetic resonance data MR1, while the object 4 undergoing investigation is positioned in a first position p1 relative to the magnetic resonance scanner. Using the first magnetic resonance data MR1 or image data ZB1 derived therefrom, a processor 8 reconstructs a first image B1 of the object 4 undergoing investigation. The first image B1 has a distortion in relation to the object 4 undergoing investigation. The processor 8 presents the first image B1 to a person 13 operating the system, at a display device 12. The processor 8 reconstructs the first image B1 such that the distortion is determined by a target position pZ that is independent of the first position p1.

The present invention has numerous advantages. It makes it possible, using magnetic resonance data MR1, MR2 that have been acquisitioned at table positions p1, p2 that may in principle be in any desired position, to determine the respective associated ND image B1, B2 for any desired other table positions pZ. Planning based on ND images is thus also possible independently of the position p1, p2 in which the associated magnetic resonance data MR1, MR2 was acquisitioned. The restrictions that are—unnecessarily—taken into account in the prior art are removed. Thus, there is no longer any need in the course of the preliminary examination or examinations to take account of the table positions p1, p2 in which the respectively associated magnetic resonance data MR1, MR2 are acquisitioned. For each individual diagnostic investigation, the table position pZ can be selected individually and in an optimum manner. Compromises that could in some cases impair image quality are no longer required.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for generating a magnetic resonance (MR) of an object, comprising:
    operating an MR data acquisition scanner in order to acquire MR data from a subject in a preliminary examination that precedes a diagnostic examination, with said subject being positioned at a position relative to the MR data acquisition scanner in said preliminary examination when said MR data are acquired;
    in a computer provided with said MR data, reconstructing image data from said MR data, said reconstructed image data forming an image of the subject that has a distortion therein relative to the subject;
    in said computer, determining a target position that is independent of said position of the subject;
    in said computer reconstructing said formed image, based on said determined target position, so as to cause said distortion in said reconstructed image to be determined by said determined target position; and
    from said computer, presenting said reconstructed image with said distortion, determined by said determined target position, at a display screen.

2. The method as claimed in claim 1 comprising:
    in said computer, reconstructing an intermediate image from said MR data and presenting said reconstructed intermediate image at said display screen; and
    in said computer, receiving a manually-made input that generates a marking in said intermediate image displayed at said display screen,
    wherein said determining said target position is based on said marking in said displayed intermediate image.

3. The method as claimed in claim 2 comprising, in said computer, reconstructing said intermediate image so as to either contain no distortion relative to the subject, or so as to contain said distortion determined by said position of the subject.

4. The method as claimed in claim 2 comprising, in said computer, determining a region based on said marking, and determining said target position using said region.

5. The method as claimed in claim 2 wherein said MR data are first MR data, said preliminary examination is a first preliminary examination, said position of the subject is a first position of the subject, and said intermediate image is a first intermediate image, and said marking is a first marking, and wherein said method comprises:
    operating said MR data acquisition scanner in a second preliminary examination in order to acquire second MR data from the subject positioned at a second position relative to the MR data acquisition scanner while said second MR data are acquired;
    in said computer, reconstructing a second intermediate image from said second MR data;
    from said computer, displaying said second intermediate image at said display screen in addition to said first intermediate image; and
    in said computer, determining a second marking for said second intermediate image that corresponds to the first marking that was made in said first intermediate image, and overlaying said second marking on said second intermediate image at said display screen.

6. The method as claimed in claim 5 comprising, in said computer, reconstructing said second intermediate image so as to either contain no distortion relative to the subject, or to contain a distortion determined by the second position of the subject.

7. The method as claimed in claim 6 comprising, in said computer, using said second MR data to reconstruct a second image of the subject, said second image containing a distortion determined by said determined target position, and, from said computer, presenting said second image at said display screen in addition to said first image.

8. The method as claimed in claim 7 wherein said computer automatically adopts the first marking as the second marking in said second image.

9. The method as claimed in claim 1 wherein determining said target position comprises automatically determining said target position using said MR data.

10. The method as claimed in claim 1 comprising, in said computer, receiving an input that designates a region from which diagnostic MR data are to be acquired in said diagnostic examination, and a predetermined excitation of nuclear spins in said region, wherein said determining said target position is based on said region and said predetermined excitation.

11. A non-transitory, computer-readable data storage medium encoded with programming instructions, said storage medium being loaded into a computer of a magnetic resonance (MR) imaging apparatus that comprises an MR data acquisition scanner, said programming instructions causing said computer to:
    operate an MR data acquisition scanner in order to acquire MR data from a subject in a preliminary examination that precedes a diagnostic examination, with said subject being positioned at a position relative to the MR data acquisition scanner in said preliminary examination when said MR data are acquired;
    reconstruct image data from said MR data, said reconstructed image data forming an image of the subject that has a distortion therein relative to the subject;
    determine a target position that is independent of said position of the subject;
    reconstruct said formed image, based on said target position, so as to cause said distortion in said reconstructed image to be determined by said determination of the target position; and
    present said reconstructed image with said distortion determined by said target position at a display screen.

12. A magnetic resonance (MR) imaging apparatus comprising:
    an MR data acquisition scanner; and
    a computer configured to:
        operate said MR data acquisition scanner in order to acquire MR data from a subject in a preliminary examination that precedes a diagnostic examination, with said subject being positioned at a position relative to the MR data acquisition scanner in said preliminary examination when said MR data are acquired;
        reconstruct image data from said MR data, said image data forming an image of the subject that has a distortion therein relative to the subject;
        determine a target position that is independent of said position of the subject;
        reconstruct said formed image, based on said target position, so as to cause said distortion in said reconstructed image to be determined by said determination of the target position; and present said reconstructed image with said distortion, determined by said target position, at a display screen.

13. A method for generating a magnetic resonance (MR) of an object, comprising:

operating an MR data acquisition scanner in order to acquire MR data from a subject in a preliminary examination that precedes a diagnostic examination, with said subject being positioned at a position relative to the MR data acquisition scanner in said preliminary examination when said MR data are acquired;

in a computer provided with said MR data, reconstructing image data from said MR data, said image data forming an image of the subject that has a distortion therein relative to the subject;

in said computer, determining a target position that is independent of said position of the subject;

said computer reconstructing said formed image, based on said determined target position, so as to cause said distortion in said reconstructed image to be determined by said determined target position;

from said computer, presenting said reconstructed image with said distortion, determined by said determined target position, at a display screen;

in said computer, receiving an input that designates a region from which diagnostic MR data are to be acquired in said diagnostic examination, and a predetermined excitation of nuclear spins in said region, wherein said target position is determined in order to cause said region to be excited according to said predetermined excitation; and positioning said subject at said determined target position, and acquiring said diagnostic MR data from the subject in said MR diagnostic examination with the subject at said determined target position.

* * * * *